US012753159B2

(12) United States Patent
Tsukamoto et al.

(10) Patent No.: US 12,753,159 B2
(45) Date of Patent: Oct. 6, 2026

(54) 3-HYDROXYADIPIC ACID 3,6-LACTONE COMPOSITION

(71) Applicant: Toray Industries, Inc., Tokyo (JP)

(72) Inventors: Daijiro Tsukamoto, Kamakura (JP); Kenji Kawamura, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 448 days.

(21) Appl. No.: 18/280,557

(22) PCT Filed: Mar. 11, 2022

(86) PCT No.: PCT/JP2022/010859

§ 371 (c)(1),
(2) Date: Sep. 6, 2023

(87) PCT Pub. No.: WO2022/191314

PCT Pub. Date: Sep. 15, 2022

(65) Prior Publication Data

US 2024/0140927 A1 May 2, 2024

(30) Foreign Application Priority Data

Mar. 12, 2021 (JP) ................................ 2021-039862

(51) Int. Cl.
*C07D 309/02* (2006.01)

(52) U.S. Cl.
CPC .................................. *C07D 309/02* (2013.01)

(58) Field of Classification Search
CPC .................................................. C07D 309/02
USPC ........................................................ 549/356
See application file for complete search history.

(56) References Cited

U.S. PATENT DOCUMENTS

| | | | |
|---|---|---|---|
| 4,599,202 | A | 7/1986 | Dockner et al. |
| 5,714,569 | A | 2/1998 | Maizumi et al. |
| 5,827,938 | A | 10/1998 | Schnurr et al. |
| 11,319,436 | B2 | 5/2022 | Tojo et al. |
| 11,629,243 | B2 | 4/2023 | Morioka et al. |
| 2009/0182070 | A1 | 7/2009 | Miyazono et al. |
| 2011/0177311 | A1 | 7/2011 | Manabe et al. |
| 2013/0158229 | A1 | 6/2013 | Fruchey et al. |
| 2015/0183703 | A1 | 7/2015 | Wong et al. |
| 2016/0347908 | A1 | 12/2016 | Müller et al. |
| 2017/0320819 | A1 | 11/2017 | Ito et al. |
| 2020/0291435 | A1 | 9/2020 | Isobe et al. |
| 2022/0162148 | A1 | 5/2022 | Nakamura et al. |

FOREIGN PATENT DOCUMENTS

| | | | |
|---|---|---|---|
| JP | S61-24555 | A | 2/1986 |
| JP | 2000-508305 | A | 6/2000 |
| JP | 2013-531657 | A | 8/2013 |
| JP | 2014-519476 | A | 8/2014 |
| JP | 2017-502128 | A | 1/2017 |
| WO | 1996/019521 | | 6/1996 |
| WO | 2007/037174 | A1 | 4/2007 |
| WO | 2010/038655 | A1 | 4/2010 |
| WO | 2015/072216 | A1 | 5/2015 |
| WO | 2015/086821 | A1 | 6/2015 |
| WO | 2016/068108 | A1 | 5/2016 |
| WO | 2019/107516 | A1 | 6/2019 |
| WO | 2019/208427 | A1 | 10/2019 |
| WO | 2020/175420 | A1 | 9/2020 |
| WO | 2021/006257 | | 1/2021 |

OTHER PUBLICATIONS

Kou-Yi Tserng et al., “Urinary 3-Hydroxyadipic Acid 3,6-Lactone: Structural Identification and Effect of Fasting in Adults and Children,” Metabolism, vol. 38, No. 8 Jul. 1989, pp. 655-661.
Ricard Herrera et al., “Characterization and degradation behavior of poly(butylene adipate-co-terephthalate)s,” Journal of Polymer Science Part A: Polymer Chemistry/vol. 40, Issue 23, Oct. 14, 2002, pp. 4141-4157 (Abstract).
Gopal Sirasani et al., “A Biocompatible Alkene Hydrogenation Merges Organic Synthesis with Microbial Metabolism,” Angewandte Chemie International Edition, vol. 53, 2014, pp. 7785-7788.
International Search Report dated May 24, 2022 in counterpart International Application No. PCT/JP2022/010859 w/English translation.
Written Opinion dated May 24, 2022 in counterpart International Application No. PCT/JP2022/010859.

*Primary Examiner* — Kahsay Habte
(74) *Attorney, Agent, or Firm* — DLA Piper LLP (US)

(57) ABSTRACT

A 3-hydroxyadipic acid-3,6-lactone composition includes 3-hydroxyadipic acid-3,6-lactone, and 3 to 30 parts by weight of α-hydromuconic acid with respect to 100 parts by weight of the 3-hydroxyadipic acid-3,6-lactone; and a method produces a 3-hydroxyadipic acid-3,6-lactone composition, the method including a step of heating 3-hydroxyadipic acid-3,6-lactone to obtain the 3-hydroxyadipic acid-3, 6-lactone composition.

4 Claims, No Drawings

3-HYDROXYADIPIC ACID 3,6-LACTONE COMPOSITION

TECHNICAL FIELD

This disclosure relates to a 3-hydroxyadipic acid-3,6-lactone composition containing, as a main component, 3-hydroxyadipic acid-3,6-lactone which is a raw material for adipic acid, a method of producing adipic acid from the 3-hydroxyadipic acid-3,6-lactone composition, and methods of producing a polyamide and a polyester using the adipic acid.

BACKGROUND

Adipic acid is a raw material monomer for polyamides and polyesters. The adipic acid can be industrially produced by nitric acid oxidation of a mixture of cyclohexanone and cyclohexanol (KA oil). However, since a large amount of dinitrogen monoxide ($N_2O$) gas, which has a high greenhouse effect, is by-produced, a method of producing adipic acid that does not by-produce dinitrogen monoxide in the production process is desired.

WO 2015/086821 discloses a process for reacting 3-hydroxyadipic acid-3,6-lactone with hydrogen in the presence of a hydrogenation catalyst to produce adipic acid without by-producing dinitrogen monoxide, and it is known that the 3-hydroxyadipic acid-3,6-lactone is a raw material for adipic acid. Angewandte Chemie International Edition, Vol. 53, pp 7785-7788 (2014) discloses that when α-hydromuconic acid is reacted with hydrogen in the presence of a hydrogenation catalyst, adipic acid is produced without by-producing dinitrogen monoxide, and it is known that the α-hydromuconic acid is a raw material for adipic acid. In addition, WO 2016/068108 discloses that a mixture of 3-hydroxyadipic acid-3,6-lactone and α-hydromuconic acid may be used as a raw material for ε-caprolactam, but does not suggest the applicability of the mixture as a raw material for adipic acid or an appropriate composition of the mixture as the raw material for adipic acid.

Metabolism, Vol. 38, No. 7, pp 655-661 (1989) discloses the relationship between fatty acid metabolism and the concentration of 3-hydroxyadipic acid-3,6-lactone in urine. In that disclosure, a reference sample of the 3-hydroxyadipic acid-3,6-lactone has been chemically synthesized for the purpose of quantifying the 3-hydroxyadipic acid-3,6-lactone in urine. It discloses a 3-hydroxyadipic acid-3,6-lactone composition in which the synthesized 3-hydroxyadipic acid-3,6-lactone contains 2 parts by weight of α-hydromuconic acid with respect to 100 parts by weight of the 3-hydroxyadipic acid-3,6-lactone, but there is neither description nor suggestion of the applicability of using the mixture as a raw material for adipic acid.

As described above, the 3-hydroxyadipic acid-3,6-lactone or the α-hydromuconic acid is known to be a raw material for adipic acid. However, we found that when pure 3-hydroxyadipic acid-3,6-lactone or α-hydromuconic acid is actually reacted with hydrogen in the presence of a hydrogenation catalyst to produce adipic acid, there is a problem that adipic acid selectivity is not sufficient.

SUMMARY

We found that a 3-hydroxyadipic acid-3,6-lactone composition in which a specific amount of α-hydromuconic acid is contained as an accessory component in 3-hydroxyadipic acid-3,6-lactone can be a good raw material for adipic acid that can prevent the production of by-products.

We thus provide (1) to (11):

(1) A 3-hydroxyadipic acid-3,6-lactone composition including:
- 3-hydroxyadipic acid-3,6-lactone; and
- 3 to 30 parts by weight of α-hydromuconic acid with respect to 100 parts by weight of the 3-hydroxyadipic acid-3,6-lactone.

(2) A method of producing a 3-hydroxyadipic acid-3,6-lactone composition, the method including:
- a step of heating 3-hydroxyadipic acid-3,6-lactone to obtain the 3-hydroxyadipic acid-3,6-lactone composition according to (1).

(3) A method of producing adipic acid, the method including:
- a step (hydrogenation step) of reacting the 3-hydroxyadipic acid-3,6-lactone composition according to (1) with hydrogen in a presence of a hydrogenation catalyst.

(4) The method of producing adipic acid according to (3), the method further including:
- a step of obtaining the 3-hydroxyadipic acid-3,6-lactone composition according to (1) by the method according to (2).

(5) A method of producing a polyamide, the method including:
- a step of producing adipic acid by the method according to (3) or (4); and
- a step of polycondensing the adipic acid and a diamine.

(6) The method of producing a polyamide according to (5), in which the diamine is a diamine including 1,4-butanediamine, 1,5-pentanediamine or hexamethylenediamine.

(7) The method of producing a polyamide according to (5) or (6), in which the polyamide is polyamide 46, polyamide 56, or polyamide 66.

(8) A method of producing a polyester, the method including:
- a step of producing adipic acid by the method according to (3) or (4); and
- a step of polycondensing the adipic acid and glycols, or the adipic acid, glycols, and a dicarboxylic acid.

(9) The method of producing a polyester according to (8), in which the glycols are glycols including 1,4-butanediol.

(10) The method of producing a polyester according to (8) or (9), in which the dicarboxylic acid is a dicarboxylic acid including terephthalic acid or succinic acid.

(11) The method of producing a polyester according to any one of (8) to (10), in which the polyester is polybutylene adipate terephthalate or polybutylene succinate adipate.

It is thus possible to increase adipic acid selectivity when producing adipic acid using 3-hydroxyadipic acid-3,6-lactone as a raw material.

DETAILED DESCRIPTION

Hereinafter, our adipic acids, lactone compositions and methods will be described in more detail.

3-Hydroxyadipic Acid-3,6-Lactone

The 3-hydroxyadipic acid-3,6-lactone is an organic compound represented by chemical formula (1), and can be chemically synthesized, for example, by a method shown in Reference Example 1 in Examples described later:

(1)

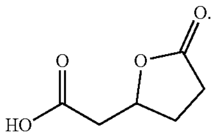

3-Hydroxyadipic acid-3, 6-lactone

In addition, the 3-hydroxyadipic acid-3,6-lactone can be synthesized by using 3-oxoadipic acid, which can be synthesized from biomass resources, as a raw material, for example, by a reaction shown in Scheme 1:

Scheme 1

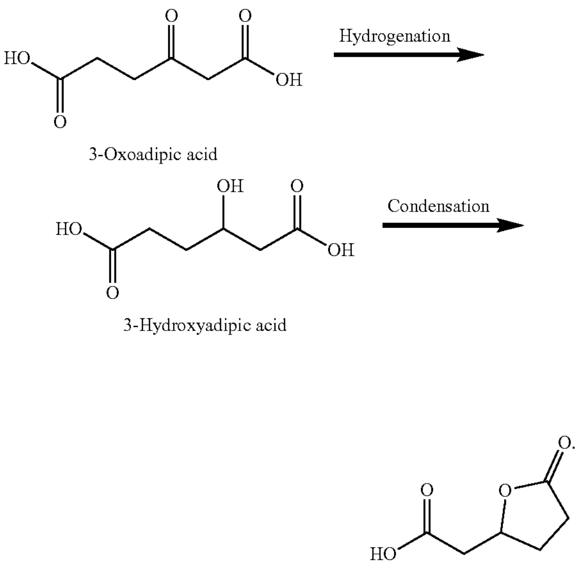

3-Oxoadipic acid

3-Hydroxyadipic acid

3-Hydroxyadipic acid-3,6-lactone

As the 3-hydroxyadipic acid-3,6-lactone, a carboxylic acid, a carboxylate salt, or a carboxylic acid ester may be used, and even a mixture thereof can be used as starting materials. These are collectively referred to herein as "3-hydroxyadipic acid-3,6-lactone."

Examples of the carboxylate salt of the 3-hydroxyadipic acid-3,6-lactone include an alkali metal salt, an alkaline earth metal salt, or an ammonium salt, and specific examples thereof include a lithium salt, a sodium salt, a potassium salt, and an ammonium salt.

Examples of the carboxylic acid ester of the 3-hydroxyadipic acid-3,6-lactone include an alkyl ester, and specific examples of the alkyl group include a methyl group, an ethyl group, an n-propyl group, an isopropyl group, an n-butyl group, an isobutyl group, and a tert-butyl group.

The 3-hydroxyadipic acid-3,6-lactone can be prepared by dissolving 3-hydroxyadipic acid represented by chemical formula (2) in water and adjusting the pH to 4 or less:

(2)

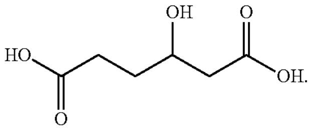

3-Hydroxyadipic acid

An acid added to adjust the pH to 4 or less is not particularly limited, and mineral acids such as sulfuric acid, hydrochloric acid, nitric acid, phosphoric acid, and boric acid, and organic acids such as formic acid, acetic acid, and propionic acid are preferably used.

α-Hydromuconic Acid

The α-hydromuconic acid is an organic compound represented by chemical formula (3), and can be chemically synthesized, for example, by a method shown in Reference Example 2 in Examples described later:

(3)

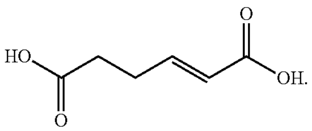

α-Hydromuconic acid

The α-hydromuconic acid can also be obtained by converting a carbon source derivable from biomass by microbial fermentation, as described in WO 2019/107516. Since the α-hydromuconic acid has one double bond in the molecule, there are cis and trans geometric isomers. In the production method, any of cis isomers, trans isomers, or mixtures of cis isomers and trans isomers can be used as the raw material.

As the α-hydromuconic acid, a carboxylic acid, a carboxylate salt, or a carboxylic acid ester may be used, and even a mixture thereof can be used as starting materials. These are collectively referred to as "α-hydromuconic acid."

Examples of the carboxylate salt of the α-hydromuconic acid include an alkali metal salt, an alkaline earth metal salt, and an ammonium salt, and specific examples thereof include a monolithium salt, a dilithium salt, a monosodium salt, a disodium salt, a monopotassium salt, a dipotassium salt, a magnesium salt, a calcium salt, a monoammonium salt, and a diammonium salt.

Examples of the carboxylic acid ester of the α-hydromuconic acid include a monoalkyl ester and a dialkyl ester, and specific examples of the alkyl group include a methyl group, an ethyl group, an n-propyl group, an isopropyl group, an n-butyl group, an isobutyl group, and a tert-butyl group.

3-Hydroxyadipic Acid-3,6-Lactone Composition

The 3-hydroxyadipic acid-3,6-lactone composition is characterized by containing 3-hydroxyadipic acid-3,6-lactone as a main component and α-hydromuconic acid as an accessory component. By using the 3-hydroxyadipic acid-3,6-lactone composition, adipic acid can be synthesized with high selectivity.

"As a main component" means that the content of the 3-hydroxyadipic acid-3,6-lactone in the 3-hydroxyadipic acid-3,6-lactone composition is more than 50 wt %, preferably 60 wt % or more, and more preferably 70 wt % or more.

In the 3-hydroxyadipic acid-3,6-lactone composition, the content of the α-hydromuconic acid with respect to 100 parts by weight of the 3-hydroxyadipic acid-3,6-lactone is 3 to 30 parts by weight, preferably 4 to 28 parts by weight, and more preferably 5 to 25 parts by weight. The composition can reduce the amount of n-valeric acid which is a by-product and thus increase the adipic acid selectivity in the production of adipic acid.

The method of producing the 3-hydroxyadipic acid-3,6-lactone composition is not particularly limited, and the composition may be prepared by mixing pure 3-hydroxyadipic acid-3,6-lactone and α-hydromuconic acid each prepared separately.

In addition, when the α-hydromuconic acid is contained as an impurity during the production of the 3-hydroxyadipic acid-3,6-lactone, the 3-hydroxyadipic acid-3,6-lactone composition may be prepared by appropriately adjusting the amount of impurities. Specifically, the α-hydromuconic acid may be generated by heating during the process of producing the 3-hydroxyadipic acid-3,6-lactone and, in this example, the content of the α-hydromuconic acid can be adjusted by appropriately adjusting the heating temperature. The higher the heating temperature, the more easily the α-hydromuconic acid is produced. However, when the heating temperature is too high, the 3-hydroxyadipic acid-3,6-lactone composition is easily thermally decomposed. From such a viewpoint, the heating temperature is preferably 100° C. to 300° C., more preferably 120° C. to 250° C., and still more preferably 150° C. to 200° C.

The 3-hydroxyadipic acid-3,6-lactone and the α-hydromuconic acid contained in the 3-hydroxyadipic acid-3,6-lactone composition can be quantified by analyzing an aqueous solution obtained by dissolving the composition in water by high performance liquid chromatography (HPLC). A conductivity detector (CDD) and a UV-Vis detector (measurement wavelength: 210 nm) are used for HPLC analysis of the 3-hydroxyadipic acid-3,6-lactone and the α-hydromuconic acid, respectively. The concentration of the composition in the aqueous solution of the 3-hydroxyadipic acid-3,6-lactone composition prepared for HPLC analysis is suitably 1 g/L to 10 g/L from the viewpoint of detection sensitivity.

The 3-hydroxyadipic acid-3,6-lactone composition may contain water, an alcohol, a carboxylic acid, an ether, an ester, and an ion as a third component other than the 3-hydroxyadipic acid-3,6-lactone and the α-hydromuconic acid. Specific examples of the alcohol include methanol, ethanol, n-propanol, isopropanol, n-butanol, isobutanol, and tert-butanol. Specific examples of the carboxylic acid include oxalic acid, acetic acid, lactic acid, formic acid, pyruvic acid, propionic acid, malonic acid, succinic acid, citric acid, glycolic acid, malic acid, n-butyric acid, isobutyric acid, hydroxybutyric acid, α-ketoglutaric acid, maleic acid, tartaric acid, glyoxylic acid, citraconic acid, pyroglutaric acid, ascorbic acid, and 3-hydroxyadipic acid. Specific examples of the ether include dimethyl ether, diethyl ether, 1,2-dimethoxyethane, diglyme, tetrahydrofuran, and dioxane. Specific examples of the ester include methyl acetate, ethyl acetate, n-propyl acetate, n-butyl acetate, and γ-butyrolactone. Specific examples of the ion include $H^+$, $Li^+$, $Na^+$, $K^+$, $NH_4^+$, $Mg^{2+}$, $Ca^{2+}$, $Fe^{2+}$, $Fe^{3+}$, $Zn^{2+}$, $Ni^{2+}$, $Mn^{2+}$, $OH^-$, $Cl^-$, $NO_3^-$, $SO_4^{2-}$, $PO_4^{3-}$, and $CO_3^{2-}$.

In the 3-hydroxyadipic acid-3,6-lactone composition, the difference between the sum of the contents of the 3-hydroxyadipic acid-3,6-lactone (main component) and the α-hydromuconic acid (accessory component) and 100 wt % is constituted by the third component. Therefore, for example, a mixture containing 75 wt % of 3-hydroxyadipic acid-3,6-lactone, 10 wt % of α-hydromuconic acid (equivalent to 13.3 parts by weight of the α-hydromuconic acid with respect to 100 parts by weight of the 3-hydroxyadipic acid-3,6-lactone), and 15 wt % of water is included in the 3-hydroxyadipic acid-3,6-lactone composition.

The third component may be of one type or multiple types, and water is preferred when the third component is contained. Specifically, when water is contained as the third component in the 3-hydroxyadipic acid-3,6-lactone composition, the content of water in the composition is preferably 40 wt % or less, more preferably 30 wt % or less, still more preferably 25 wt % or less, and particularly preferably 20 wt % or less, with respect to 100 wt % of the 3-hydroxyadipic acid-3,6-lactone composition.

Production of Adipic Acid

The adipic acid can be produced by reacting (hydrogenating) the 3-hydroxyadipic acid-3,6-lactone composition with hydrogen in the presence of a hydrogenation catalyst.

The hydrogenation catalyst preferably contains a transition metal element, specifically preferably contains one or two or more selected from the group consisting of palladium, platinum, ruthenium, rhodium, rhenium, nickel, cobalt, iron, iridium, osmium, copper, and chromium, and more preferably contains one or two or more selected from the group consisting of palladium, platinum, nickel, cobalt, iron, copper, and chromium.

The hydrogenation catalyst is preferably supported on a carrier from the viewpoint of saving the amount of metal used and increasing the active surface of the catalyst. Supporting of the hydrogenation catalyst on the carrier can be carried out by known methods such as an impregnation method, a deposition precipitation method, and a vapor phase support method. Examples of the carrier include carbon, polymers, metal oxides, metal sulfides, zeolites, clays, heteropolyacids, solid phosphoric acid, and hydroxyapatite.

Hydrogen to be reacted with the 3-hydroxyadipic acid-3,6-lactone composition may be added all at once or sequentially to the reactor. The partial pressure of hydrogen is not particularly limited, and when it is too low, the reaction time is longer, and when the partial pressure of hydrogen is too high, it is undesirable in terms of equipment safety. Therefore, the partial pressure of hydrogen is preferably 0.1 MPa or more and 10 MPa or less (gauge pressure), more preferably 0.3 MPa or more and 5 MPa or less (gauge pressure), and still more preferably 0.5 MPa or more and 3 MPa or less (gauge pressure) at room temperature.

The reaction form may be a reaction form using any of a batch type tank reactor, a semi-batch type tank reactor, a continuous tank reactor, a continuous tubular reactor, and a trickle bed tubular reactor. When a solid hydrogenation catalyst is used, the reaction can be carried out in any of suspended bed, fixed bed, moving bed and fluidized bed systems.

The reaction temperature in hydrogenation is not particularly limited, and when it is too low, the reaction rate becomes slow, and when the reaction temperature is too high, energy consumption increases, which is not preferred. From such a viewpoint, the reaction temperature is preferably 100° C. to 350° C., more preferably 120° C. to 300° C., still more preferably 130° C. to 280° C., even more preferably 140° C. to 250° C., even still more preferably 150° C. to 230° C., and further even still more preferably 160° C. to 220° C.

As the atmosphere in the reactor, in addition to hydrogen, an inert gas such as nitrogen, helium or argon may coexist, and the oxygen concentration is preferably 5 vol % or less because it leads to deterioration of the hydrogenation catalyst and generation of detonation gas. In addition, from the viewpoint of the stability of the 3-hydroxyadipic acid-3,6-lactone composition and the adipic acid, the amount of ammonia to the 3-hydroxyadipic acid-3,6-lactone composition is preferably 5 wt % or less, more preferably 3 wt % or less, and still more preferably 0 wt % (that is, the reaction in the absence of ammonia).

The hydrogenation of the 3-hydroxyadipic acid-3,6-lactone composition is preferably carried out in the presence of a solvent.

As the solvent in the hydrogenation, methanol, ethanol, n-propanol, isopropanol, n-butanol, isobutanol, tert-butanol, pentane, hexane, cyclohexane, heptane, octane, decane, dimethyl ether, diethyl ether, 1,2-dimethoxyethane, diglyme, tetrahydrofuran, dioxane, methyl acetate, ethyl acetate, n-propyl acetate, n-butyl acetate, γ-butyrolactone, N-methylpyrrolidone, dimethylsulfoxide, aqueous solvents, or the like can be used. A mixed solvent of two or more of these may be used, and it is preferable to use an aqueous solvent from the viewpoint of economy and environmental friendliness.

The term "aqueous solvent" means water or a mixed solvent containing water as a main component and a water-miscible organic solvent. The expression "containing water as a main component" means that the ratio of water in the mixed solvent is more than 50 vol %, preferably 70 vol % or more, and more preferably 90 vol % or more.

Examples of the water-miscible organic solvent include methanol, ethanol, n-propanol, isopropanol, n-butanol, isobutanol, tert-butanol, 1,2-dimethoxyethane, diglyme, tetrahydrofuran, dioxane, γ-butyrolactone, N-methylpyrrolidone, dimethylsulfoxide, dimethylformamide, dimethylacetamide, and acetone.

The pH of the aqueous solvent is not particularly limited, and considering the prevention of catalyst deterioration, prevention of by-product formation, corrosiveness to the reactor, the pH is preferably 2 to 13, more preferably 3 to 11, and still more preferably 4 to 10.

The amount of the 3-hydroxyadipic acid-3,6-lactone composition to be added with respect to the solvent is not particularly limited, and when the amount to be added is small, it is not industrially preferred. From such a viewpoint, the amount of the 3-hydroxyadipic acid-3,6-lactone composition to be added with respect to 100 parts by weight of the solvent is preferably 0.1 parts by weight or more and 900 parts by weight or less, more preferably 0.2 parts by weight or more and 800 parts by weight or less, and still more preferably 1.0 parts by weight or more and 700 parts by weight or less, as an equivalent amount of the 3-hydroxyadipic acid-3,6-lactone.

When a solvent other than a primary alcohol and a secondary alcohol is used as the solvent in the hydrogenation, adipic acid, an adipate salt, and an adipic acid ester are correspondingly produced from a carboxylic acid, a carboxylate salt and a carboxylic acid ester of the 3-hydroxyadipic acid-3,6-lactone composition, respectively. When a solvent including a primary alcohol or secondary alcohol such as methanol, ethanol, n-propanol, isopropanol, n-butanol, or isobutanol is used as the solvent in the hydrogenation, a mixture of adipic acid, an adipate salt, an adipic acid monoester, and an adipic acid diester is obtained after the reaction. Regarding the adipic acid, a carboxylic acid, a carboxylate salt, a carboxylic acid ester, and a mixture thereof are collectively referred to as "adipic acid."

The carboxylic acid, i.e., adipic acid obtained can be further converted into an adipic acid ester by performing an esterification reaction. The esterification method is not particularly limited, and examples thereof include dehydration condensation of a carboxylic acid and an alcohol using an acid catalyst and a condensing agent, and methods using alkylating reagents such as diazomethane and an alkyl halide.

The adipic acid obtained can be separated and purified by general unit operations such as centrifugation, filtration, membrane filtration, distillation, extraction, crystallization, and drying.

Production of Various Chemicals Using Adipic Acid as Raw Material

Adiponitrile can be produced from our adipic acid obtained by a known method (for example, JPS61-24555B). Hexamethylenediamine can be produced by hydrogenating the obtained adiponitrile by a known method (for example, JP2000-508305A).

A polyamide can be produced by polycondensing our adipic acid obtained with a diamine by a known method (see, for example, Osamu Fukumoto, "Polyamide Resin Handbook" Nikkan Kogyo Publishing Co., Ltd. (January 1998)). Specifically, by using 1,4-diaminobutane, 1,5-pentanediamine, and hexamethylenediamine as the diamine, polyamide 46, polyamide 56, and polyamide 66 can be produced, respectively.

The polyamide can be processed by a known method (for example, WO 2019/208427) to produce polyamide fibers. The polyamide fibers thus obtained can be used for clothing applications such as innerwear, sportswear and casual wear, and for industrial material applications such as airbags and tire cords.

In addition, a polyamide molded article can be produced by molding the polyamide by a known method (for example, WO 2021/006257). The polyamide molded article thus obtained can be used for automobile parts, electric parts, electronic parts, construction members, various containers, daily necessities, household goods, sanitary goods and the like.

A polyester can be produced by polycondensing our adipic acid obtained with glycols by a known method (see, for example, "Paint Research, vol. 151, p 2-8" Kansai Paint Co., Ltd. (November 2009)). Specifically, as the glycols, ethylene glycol, 1,3-propanediol, 1,4-butanediol, 1,6-hexanediol, neopentyl glycol, 3-methyl-1,5-pentanediol, 2-methyl-1,3-propanediol or the like can be used. At this time, in addition to our adipic acid obtained, any dicarboxylic acid may be copolymerized. Specifically, examples of the dicarboxylic acid to be copolymerized include oxalic acid, malonic acid, succinic acid, glutaric acid, suberic acid, sebacic acid, cyclohexanedicarboxylic acid, terephthalic acid, isophthalic acid, naphthalenedicarboxylic acid, diphenyldicarboxylic acid, and 2,5-furandicarboxylic acid. By using 1,4-butanediol as the diol and terephthalic acid or succinic acid as the dicarboxylic acid, polybutylene adipate terephthalate (PBAT) and polybutylene succinate adipate (PBSA) can be obtained, respectively. These polyesters are preferred from the viewpoint of environmental friendliness because of having biodegradability. Polybutylene adipate terephthalate (PBAT) and polybutylene succinate adipate (PBSA) can be produced by known methods (for example, Journal of Polymer Science: Part A: Polymer Chemistry, vol. 40, p 4141-4157 (2002) or WO 1996/019521). The term "biodegradebility" refers to the property of being decomposed down to the molecular level by the action of microorganisms, and finally becoming carbon dioxide and water, which circulate in the natural world.

The polyester can be processed by a known method (for example, WO 2007/037174) to produce polyester fibers. The polyester fibers thus obtained can be made into fiber products such as woven fabrics, knitted fabrics and non-woven fabrics, and can also be made into clothing, fiber brushes, rugs and the like using them.

In addition, a polyester molded article can be produced by molding the polyester by a known method (for example, WO 2015/072216). The polyester molded article thus obtained can be used for automobile parts, electric parts, electronic parts, mechanical parts, construction members, various containers, daily necessities, household goods, sanitary goods and the like.

The polyester can be stretched by a known method (for example, WO 2010/038655) to produce a polyester film. The polyester film thus obtained can be used in a wide variety of applications such as electronic equipment, semiconductor products, electric products, automobile parts, packaging applications, and building materials.

Examples

Hereinafter, our adipic acids, lactone compositions and methods will be described in more detail using Examples, but this disclosure is not limited to the following Examples. The reaction results in Examples and Comparative Examples are defined by the following equations:

Product selectivity (%)=product yield (mol)/reacted raw material (mol)×100.

Analysis and quantification of 3-hydroxyadipic acid-3,6-lactone and adipic acid were carried out under the following HPLC analysis conditions 1. Analysis and quantification of α-hydromuconic acid and n-valeric acid were carried out under the following HPLC analysis conditions 2. Quantification of raw materials and products was carried out using an absolute calibration curve prepared using a standard.

HPLC Analysis Conditions 1

- HPLC device: "Prominence" (manufactured by Shimadzu Corporation)
- Column: "Synergi Polar-RP" (manufactured by Phenomenex), length: 250 mm, inner diameter: 4.60 mm, particle size: 4 μm+"Synergi hydro-RP" (manufactured by Phenomenex), length: 250 mm, inner diameter: 4.60 mm, particle size: 4 μm
- Mobile phase: 5 mM formic acid aqueous solution/acetonitrile=98/2 (volume ratio)
- Reaction solution: 5 mM formic acid+20 mM Bis-Tris+0.1 mM EDTA·2Na aqueous solution/acetonitrile=98/2 (volume ratio)
- Flow rate: 1.0 mL/min
- Detector: conductivity detector (CDD)
- Column temperature: 45° C.

HPLC Analysis Conditions 2

- HPLC device: "Prominence" (manufactured by Shimadzu Corporation)
- Column: "Synergi hydro-RP" (manufactured by Phenomenex), length: 250 mm, inner diameter: 4.60 mm, particle size: 4 μm
- Mobile phase: 0.1 wt % phosphoric acid aqueous solution/acetonitrile=95/5 (volume ratio)
- Flow rate: 1.0 mL/min
- Detector: UV-Vis detector (measurement wavelength: 210 nm)
- Column temperature: 40° C.

pH Analysis Method

A Horiba pH meter F-52 (manufactured by Horiba, Ltd.) was used. pH calibration was carried out by using a pH 4.01 standard solution (manufactured by FUJIFILM Wako Pure Chemical Corporation), a pH 6.86 standard solution (manufactured by FUJIFILM Wako Pure Chemical Corporation), and a pH 9.18 standard solution (manufactured by FUJIFILM Wako Pure Chemical Corporation).

Reference Example 1

Chemical Synthesis of 3-Hydroxyadipic Acid-3,6-Lactone

The 3-hydroxyadipic acid-3,6-lactone was prepared by chemical synthesis. First, 1.5 L of ultra-dehydrated tetrahydrofuran (manufactured by FUJIFILM Wako Pure Chemical Corporation) was added to 13.2 g (0.1 mol) of monomethyl ester succinate (manufactured by FUJIFILM Wako Pure Chemical Corporation), and 16.2 g (0.1 mol) of carbonyldiimidazole (manufactured by FUJIFILM Wako Pure Chemical Corporation) was added with stirring, followed by stirring at room temperature for 1 hour under a nitrogen atmosphere. To this suspension, 15.6 g (0.1 mol) of malonic acid monomethyl ester potassium salt and 9.5 g (0.1 mol) of magnesium chloride were added, followed by stirring at room temperature for 1 hour under nitrogen atmosphere, and then the mixture was stirred at 40° C. for 12 hours. After completion of the reaction, 0.05 L of 1 mol/L hydrochloric acid was added, and extraction with ethyl acetate and separation and purification with silica gel column chromatography (hexane:ethyl acetate=1:5) were conducted to obtain 13.1 g of pure 3-oxohexanedicarboxylic acid dimethyl ester.

To 10 g (0.05 mol) of the obtained 3-oxohexanedicarboxylic acid dimethyl ester, 0.1 L of methanol (manufactured by KOKUSAN CHEMICAL CO., LTD.) was added, and 0.02 L of a 5 mol/L sodium hydroxide aqueous solution was added with stirring, followed by stirring at room temperature for 2 hours. After completion of the reaction, the pH was adjusted to 1 with 5 mol/L hydrochloric acid, and then 2.0 g (0.05 mol) of sodium borohydride (manufactured by FUJIFILM Wako Pure Chemical Corporation) was added, followed by stirring at room temperature for 2 hours. After concentration with a rotary evaporator, 0.1 L of ultrapure water was added, and 0.01 L of 1 mol/L sulfuric acid was added with stirring, followed by stirring at 100° C. for 2 hours. This solution was concentrated by a rotary evaporator and then separated and purified by silica gel column chromatography (chloroform:methanol=10:1) to obtain 5.8 g of pure 3-hydroxyadipic acid-3,6-lactone (carboxylic acid).

$^1$H-NMR (400 MHz, $D_2O$): δ2.03 (m, 1H), δ2.04-2.90 (m, 5H), δ5.00 (m, 1H).

Reference Example 2

Chemical Synthesis of α-Hydromuconic Acid

The α-hydromuconic acid was prepared by chemical synthesis. To 10 g (0.05 mol) of the 3-oxohexanedicarboxylic acid dimethyl ester obtained in the same manner as in Reference Example 1, 0.1 L of methanol (manufactured by KOKUSAN CHEMICAL CO., LTD.) was added, and 2.0 g (0.05 mol) of sodium borohydride (manufactured by FUJIFILM Wako Pure Chemical Industries, Ltd.) was added while stirring, followed by stirring at room temperature for 1 hour. Next, 0.02 L of 5 mol/L sodium hydroxide aqueous solution was added, followed by stirring at room temperature for 2 hours. After completion of the reaction, the pH was adjusted to 1 with 5 mol/L hydrochloric acid. After concentration with a rotary evaporator, recrystallization with water was conducted to obtain 7.2 g of pure α-hydromuconic acid (carboxylic acid).

$^1$H-NMR (400 MHz, $CD_3OD$): δ2.48 (m, 4H), δ5.84 (d, 1H), δ6.96 (m, 1H).

Reference Example 3

Chemical Synthesis of 3-Hydroxyadipic Acid

The 3-hydroxyadipic acid was prepared by chemical synthesis. To 10 g (0.05 mol) of the obtained 3-oxohexanedicarboxylic acid dimethyl ester obtained in the same manner as in Reference Example 1, 0.1 L of methanol (manufactured by KOKUSAN CHEMICAL CO., LTD.) was added, and 0.02 L of a 5 mol/L sodium hydroxide aqueous solution was added with stirring, followed by stirring at room temperature for 2 hours. After completion of the reaction, the pH was adjusted to 1 with 5 mol/L hydrochloric acid, and then 2.0 g (0.05 mol) of sodium borohydride (manufactured by FUJIFILM Wako Pure Chemical Industries, Ltd.) was added, followed by stirring at room temperature for 2 hours. After completion of the reaction, concentration with a rotary evaporator was conducted and then recrystallization with water was conducted to obtain 7.2 g of pure 3-hydroxyadipic acid (carboxylic acid).

$^1$H-NMR (400 MHz, $CD_3OD$): δ1.70 (m, 1H), δ1.83 (m, 1H), δ2.42 (m, 4H), δ4.01 (m, 1H).

Example 1

0.92 g of the 3-hydroxyadipic acid-3,6-lactone (carboxylic acid) prepared in Reference Example 1 was physically mixed with 0.08 g of the α-hydromuconic acid (carboxylic acid) prepared in Reference Example 2, to obtain a 3-hydroxyadipic acid-3,6-lactone composition containing 8.7 parts by weight of α-hydromuconic acid with respect to 100 parts by weight of 3-hydroxyadipic acid-3,6-lactone.

To a stainless steel autoclave having an internal capacity of 0.1 L (manufactured by Taiatsu Glass Industry Co., Ltd.), 1.0 g of the above 3-hydroxyadipic acid-3,6-lactone composition, 20 g of water, and 0.025 g of Palladium, 5% on gamma alumina powder, reduced (manufactured by Alfa Aesar) were added. After purging the inside of the autoclave with nitrogen, hydrogen gas was added to adjust the hydrogen partial pressure inside the autoclave to 0.9 MPa (gauge pressure). The temperature inside the autoclave was raised to 200° C., maintained at 200° C. for 3 hours, and then allowed to cool to room temperature, the gas inside the autoclave was released to return the pressure to normal pressure, and the reaction solution was recovered. The filtrate from which the catalyst was removed by filtration was analyzed by HPLC and the product selectivity was calculated. The results are shown in Table 1.

Example 2

The 3-hydroxyadipic acid-3,6-lactone (carboxylic acid) (0.8 g) prepared in Reference Example 1 was physically mixed with 0.2 g of the α-hydromuconic acid (carboxylic acid) prepared in Reference Example 2, to obtain a 3-hydroxyadipic acid-3,6-lactone composition containing 25 parts by weight of α-hydromuconic acid with respect to 100 parts by weight of 3-hydroxyadipic acid-3,6-lactone, and a reaction was carried out in the same manner as in Example 1. The results are shown in Table 1.

Comparative Example 1

A reaction was carried out in the same manner as in Example 1, except that 1 g of the 3-hydroxyadipic acid-3,6-lactone (carboxylic acid) prepared in Reference Example 1 was used instead of the 3-hydroxyadipic acid-3,6-lactone composition. The results are shown in Table 1.

Comparative Example 2

A reaction was carried out in the same manner as in Example 1, except that 1 g of the α-hydromuconic acid (carboxylic acid) prepared in Reference Example 2 was used instead of the 3-hydroxyadipic acid-3,6-lactone composition. The results are shown in Table 1.

Example 3

3 g of the 3-hydroxyadipic acid-3,6-lactone (carboxylic acid) prepared in Reference Example 1 was added to an eggplant flask, followed by heating to 165° C. in an oil bath, maintaining at 165° C. for 30 minutes, and then cooling to room temperature. An aqueous solution obtained by adding 300 mL of water into the eggplant flask was analyzed by HPLC. The content of the α-hydromuconic acid in the aqueous solution was 5.9 parts by weight with respect to 100 parts by weight of the 3-hydroxyadipic acid-3,6-lactone. A reaction was carried out in the same manner as in Example 1 using 1 g of the 3-hydroxyadipic acid-3,6-lactone composition obtained by removing water with a rotary evaporator. The results are shown in Table 1.

TABLE 1

Production of adipic acid from 3-hydroxyadipic acid-3,6-lactone composition

| | Content (part by weight) of αHMA with respect to 100 parts by weight of 3HAL | Solvent | Reaction temperature (° C.) | Adipic acid selectivity (%) | n-valeric acid selectivity (%) |
|---|---|---|---|---|---|
| Example 1 | 8.7 | Water | 200 | 93.3 | 4.5 |
| Example 2 | 25.0 | Water | 200 | 93.8 | 4.5 |
| Example 3 | 5.9 | Water | 200 | 93.6 | 4.6 |
| Comparative Example 1 | 0 | Water | 200 | 87.0 | 9.5 |
| Comparative Example 2 | ∞ (only αHMA) | Water | 200 | 83.5 | 10.6 |

3HAL: 3-hydroxyadipic acid-3,6-lactone
α-HMA: α-hydromuconic acid

It is suggested from Examples 1 to 3 and Comparative Examples 1 and 2 that compared to using pure 3-hydroxyadipic acid-3,6-lactone or pure α-hydromuconic acid as a raw material, production of n-valeric acid, which is a by-product, is prevented, and adipic acid can be produced with high selectivity by using, as a raw material, a 3-hydroxyadipic acid-3,6-lactone composition containing 3 to 30 parts by weight of α-hydromuconic acid with respect to 100 parts by weight of 3-hydroxyadipic acid-3,6-lactone.

Comparative Example 3

0.98 g of the 3-hydroxyadipic acid-3,6-lactone (carboxylic acid) prepared in Reference Example 1 was physically mixed with 0.02 g of the α-hydromuconic acid (carboxylic acid) prepared in Reference Example 2, to obtain a 3-hydroxyadipic acid-3,6-lactone composition containing 2 parts by weight of α-hydromuconic acid with respect to 100 parts by weight of 3-hydroxyadipic acid-3,6-lactone, and a reaction was carried out in the same manner as in Example 1. The results are shown in Table 2.

Example 4

3 g of the 3-hydroxyadipic acid-3,6-lactone (carboxylic acid) prepared in Reference Example 1 was added to an eggplant flask, followed by heating to 190° C. in an oil bath, maintaining at 190° C. for 30 minutes, and then cooling to room temperature. An aqueous solution obtained by adding 300 mL of water into the eggplant flask was analyzed by HPLC. The content of the α-hydromuconic acid in the aqueous solution was 11 parts by weight with respect to 100 parts by weight of the 3-hydroxyadipic acid-3,6-lactone. A reaction was carried out in the same manner as in Example 1 using 1 g of the 3-hydroxyadipic acid-3,6-lactone composition obtained by removing water with a rotary evaporator. The results are shown in Table 2.

Example 5

0.9 g of the 3-hydroxyadipic acid-3,6-lactone (carboxylic acid) prepared in Reference Example 1 was physically mixed with 0.1 g of the α-hydromuconic acid (carboxylic acid) prepared in Reference Example 2, to obtain a 3-hydroxyadipic acid-3,6-lactone composition containing 11.1 parts by weight of α-hydromuconic acid with respect to 100 parts by weight of 3-hydroxyadipic acid-3,6-lactone, and a reaction was carried out in the same manner as in Example 1, except that 0.005 g of 5% palladium/carbon (manufactured by FUJIFILM Wako Pure Chemical Industries, Ltd.) was used as a catalyst, and the reaction temperature was set to 160° C. The results are shown in Table 2.

Example 6

A reaction was carried out in the same manner as in Example 1, except that tetrahydrofuran (THF) was used as the solvent instead of water. The results are shown in Table 2.

Example 7

A reaction was carried out in the same manner as in Example 1, except that a mixed solvent of water and tetrahydrofuran (water/THF: 6/4 v/v) was used instead of water. The results are shown in Table 2.

Example 8

20 g of the 3-hydroxyadipic acid-3,6-lactone (carboxylic acid) prepared in Reference Example 1 was added to an eggplant flask, followed by heating to 200° C. in an oil bath, maintaining at 200° C. for 30 minutes, and then cooling to room temperature, to obtain a 3-hydroxyadipic acid-3,6-lactone composition containing 8.6 parts by weight of α-hydromuconic acid with respect to 100 parts by weight of 3-hydroxyadipic acid-3,6-lactone.

To a stainless steel autoclave having an internal capacity of 0.1 L (manufactured by Taiatsu Glass Industry Co., Ltd.), 10 g of the above 3-hydroxyadipic acid-3,6-lactone composition, 20 g of water, and 0.02 g of 5% palladium carbon (FUJIFILM Wako Pure Chemical Industries, Ltd.) were added. After purging the inside of the autoclave with nitrogen, the pressure inside the autoclave was maintained at 0.9 MPa (gauge pressure) during the hydrogenation by pressurizing with hydrogen gas. The temperature was raised to 150° C., maintained at 150° C. for 15 hours, and then allowed to cool to room temperature, the gas inside the autoclave was released to return the pressure to normal pressure, and the reaction solution was recovered. The filtrate from which the catalyst was removed by filtration was analyzed by HPLC and the product selectivity was calculated. The results are shown in Table 2.

Example 9

A reaction was carried out in the same manner as in Example 1, except that 0.05 g of Raney nickel (manufactured by FUJIFILM Wako Pure Chemical Industries, Ltd.) was used as the catalyst. The results are shown in Table 2.

TABLE 2

Production of adipic acid from 3-hydroxyadipic acid-3,6-lactone composition

| | Content (part by weight) of αHMA with respect to 100 parts by weight of 3HAL | Solvent | Reaction temperature (° C.) | Adipic acid selectivity (%) | n-valeric acid selectivity (%) |
|---|---|---|---|---|---|
| Comparative Example 3 | 2.0 | Water | 200 | 88.1 | 9.9 |
| Example 4 | 11.0 | Water | 200 | 94.1 | 4.2 |
| Example 5 | 11.1 | Water | 160 | 95.5 | 3.1 |
| Example 6 | 8.7 | THF | 200 | 96.3 | 2.1 |
| Example 7 | 8.7 | Water/THF 6/4 v/v | 200 | 95.1 | 2.7 |
| Example 8 | 8.6 | Water | 150 | 98.8 | Not detected |
| Example 9 | 8.7 | Water | 200 | 92.1 | 4.6 |

3HAL: 3-hydroxyadipic acid-3,6-lactone
α-HMA: α-hydromuconic acid
THF: tetrahydrofuran It is suggested from Comparative Example 3 and Examples 4 to 9 that even with various solvents, reaction temperatures and catalysts, production of n-valeric acid, which is a by-product, is prevented, and adipic acid can be produced with high selectivity by using, as a raw material, a 3-hydroxyadipic acid-3,6-lactone composition containing 3 to 30 parts by weight of α-hydromuconic acid with respect to 100 parts by weight of 3-hydroxyadipic acid-3,6-lactone.

What is claimed is:

1. A 3-hydroxyadipic acid-3,6-lactone composition comprising:

3-hydroxyadipic acid-3,6-lactone; and 3 to 30 parts by weight of α-hydromuconic acid with respect to 100 parts by weight of the 3-hydroxyadipic acid-3,6-lactone.

2. A method of producing a 3-hydroxyadipic acid-3,6-lactone composition, the method comprising:

heating 3-hydroxyadipic acid-3,6-lactone to obtain the 3-hydroxyadipic acid-3,6-lactone composition according to claim 1.

3. A method of producing adipic acid, the method comprising:

a hydrogenation step of reacting the 3-hydroxyadipic acid-3,6-lactone composition according to claim 1 with hydrogen in a presence of a hydrogenation catalyst.

4. The method according to claim 3, further comprising:

obtaining the 3-hydroxyadipic acid-3,6-lactone composition comprising:

3-hydroxyadipic acid-3,6-lactone; and 3 to 30 parts by weight of α-hydromuconic acid with respect to 100 parts by weight of the 3-hydroxyadipic acid-3,6-lactone;

by a method comprising heating the 3-hydroxyadipic acid-3,6-lactone to obtain the 3-hydroxyadipic acid-3,6-lactone composition.

* * * * *